United States Patent [19]

Irikura et al.

[11] Patent Number: 4,735,954

[45] Date of Patent: Apr. 5, 1988

[54] ANTI-RHEUMATIC AGENT

[75] Inventors: Tsutomu Irikura, Tokyo; Keigo Nishino; Saburo Hara, both of Saitama, all of Japan

[73] Assignee: Kyorin Seiyaku Kabushiki Kaisha, Tokyo, Japan

[21] Appl. No.: 905,575

[22] Filed: Sep. 9, 1986

[30] Foreign Application Priority Data

Sep. 14, 1985 [JP] Japan .................................. 60-203765

[51] Int. Cl.$^4$ ............................................. A61K 31/44
[52] U.S. Cl. .................................................... 514/332
[58] Field of Search ......................................... 514/332

[56] References Cited

PUBLICATIONS

Chem. Abst.—102–72,579t, (1985), Sunada.
Chem. Abst.—103–64597c, (1985), Kudo.

Primary Examiner—Stanley J. Friedman
Attorney, Agent, or Firm—Jules E. Goldberg

[57] ABSTRACT

Novel anti-rheumatic agent containing 3-isobutyryl-2-isopropylpyrazolo[1,5-a]pyridine as an active ingredient.

2 Claims, No Drawings

ANTI-RHEUMATIC AGENT

BACKGROUND OF THE INVENTION 3-isobutyryl-2-isopropylpyrazalo[1,5-a]pyridine (code No. KC-404) having a chemical structure shown below was invented by the present inventors and is a publicly known compound as disclosed in Japanese Patent Publication No. Sho 52-29318; U.S. Pat. No. 3,850,941; Brit. Pat. No. 1,378,375; German Pat. No. 2,315,801 and etc. Cerebral vasodilating and bronchodilating effects of KC-404 have been disclosed in the above patents. Our studies on KC-404 revealed that it has an inhibitory effect on the type I (immediate type) allergic reaction (The Japanese Journal of Pharmacology 33, 267–278, 1983; Folia pharmacologica japonica 83, 281–289, 1984; ibid. 83, 291–299, 1984). We found that KC-404 also inhibits the Arthus reaction (type III allergic reaction) in a series of the experiments to determine its effects on type II-IV allergic reactions (Folia pharmacologica japonica 83, 291–299, 1984). It is generally accepted that the drug possessing the ability to inhibit articular rheumatism is effective in the Arthus reaction. Thus, our continuous studies on KC-404 lead us to the present invention.

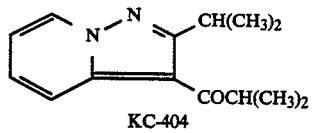

KC-404

Articular rheumatism is a progressive disease with consequent economic disability, despite intensive treatment with rest, physical therapy, gold, salicylates, and other drugs. If the patient is severely ill and has fever, joint swelling, and intense pain, many expert physicians advise administration of corticosteroids without delay. The decision of embark upon a program of hormone therapy must be made with due consideration for the fact that corticosteroid therapy, once started, may have to be continued for many years or for life, with the attendant risks of serious complications such as fluid and electrolyte disturbances, susceptibility to infections, peptic ulcers, osteoporosis, a characteristic myopathy, psychosis, and Cushing's syndromes. The initial dose of corticosteroid should be small and increased slowly until the desired degree of control is attained. The symptomatic effect of small reductions should be frequently tested in order to maintain the dose as low as possible. Complete relief, however, is not sought. Thus, in the place of corticosteroid therapy or for the reduction of dose of corticosteroids, another useful anti-rheumatic agent, surely effective and safe, has been required.

SUMMARY OF THE INVENTION

The object of the present invention is to give a certain novel anti-rheumatic agent containing KC-404 which is effective for the articular rheumatism and causes no serious complications.

DETAILED DESCRIPTION OF THE INVENTION

This invention has been achieved by our discovery of the prominent effect of KC-404 on adjuvant-induced arthritis which is an experimental model of the articular rheumatism. As shown in Experiment 1, KC-404 markedly inhibits the production of adjuvant-induced experimental arthritis in rats at the oral dose level of 20 mg/kg once or 10 mg/kg twice every day. The results in Experiment 1 are predictable for the clinical effects of KC-404. In addition, toxicological studies on KC-404 conducted in rats and mice, namely acute toxicity tests by several routes of administration (Experiment 2), subacute toxicity tests by oral administration for one month, and chronic toxicity tests by oral administration for six months revealed that KC-404 is low in toxicity. These results are supporting the safety of KC-404 for the clinical use.

The anti-rheumatic agent of the present invention may be used in the conventional form of pharmaceutical preparations, which may be, for example, tablets, capsules, powder, granules, injections, suppositories, ointment, cream, suitable for oral, parenteral, enteral or local administration. The pharmaceutical formulations of the present invention may be prepared using known technical skill in the art.

The anti-rheumatic agent of the present invention may contain KC-404 in a certain amount. Preferable amount of KC-404 is 1-500 mg per day at one time or in divided doses and can be adjusted according to the severity of articular rheumatism and to the age of patients.

The following examples will further illustrate the present invention without, however, limiting it thereto.

DESCRIPTION OF PREFERRED EMBODIMENTS

EXAMPLE 1

A mixture of 4,800 g of lactose and 1,200 g of Avicel ® (crystalline cellulose) was kneaded with 1,800 g of 2.5% aqueous solution of HPC-L (low molecular weight hydroxypropylcellulose). The resulting moist mass was granulated and dried to produce a core granule having a diameter of 0.5–0.71 mm. Onto the core granules thus obtained, 3,000 g of ethanol solution containing 200 g of KC-404 and 40 g of Eudragit L ® (an anionic polymer synthesized from methacrylic acid and methacrylic acid methyl ester, soluble in intestinal juice from pH 6 upwards) was sprayed in a fluidized bed coating apparatus (Spira-cota ®) to form a conventional granule.

EXAMPLE 2

1,900 g of the granules obtained in Example 1 was coated with 580 g of 3.3% ethanol solution of Eudragit S ® (an anionic polymer synthesized from methacrylic acid and methacrylic acid methyl ester, soluble in intestinal juice from pH 7 upwards) in the same apparatus to give a controlled-release granule.

Experiment 1

Eight female Wistar rats in each group, weighing 140–200 g were used. The arthritis was induced by intradermal injection of *Mycobacterium butyricum* suspended in liquid paraffin (0.6 mg/0.1 ml) as the adjuvant to tail. The change in volume of both legs due to the formation of edema was measured 12, 16 and 19 days after the adjuvant challenge. In addition, a severity of the secondary inflammation observed in auricles, paws, legs and tail was graded into the degrees of 0–4. KC-404 or hydrocortisone was orally administered every day (excepting Sunday) for 19 days including the day of the adjuvant injection. The results of experiment were given in Tables 1, 2 and 3.

TABLE 1

Inhibitory Effects of Orally Administered Present Compound and Hydrocortisone on Adjuvant-induced Edema in Left Legs

| Compounds | Dose (mg/kg/day) | Inhibition (%) | | |
|---|---|---|---|---|
| | | 12th | 16th | 19th day |
| KC-404 | 20 | 71.7 | 79.9*** | 61.1** |
| | 10 × 2 | 50.2 | 28.6 | 41.9*** |
| Hydrocortisone | 5 | 57.0 | 53.1 | 54.7** |

**$P < 0.02$,
***$P < 0.01$.

TABLE 2

Inhibitory Effects of Orally Administered Present Compound and Hydrocortisone on Adjuvant-induced Edema in Right Legs

| Compounds | Dose (mg/kg/day) | Inhibition (%) | | |
|---|---|---|---|---|
| | | 12th | 16th | 19th day |
| KC-404 | 20 | 44.4 | 80.8 | 53.1*** |
| | 10 × 2 | 19.8 | 56.6 | 39.9** |
| Hydrocortisone | 5 | 90.9 | 60.1* | 57.8*** |

*$P < 0.05$,
**$P < 0.02$,
***$P < 0.01$.

TABLE 3

Inhibitory Effects of Orally Administered Present Compound and Hydrocortisone on Adjuvant-induced Secondary Inflammation

| Compounds | Dose (mg/kg/day) | Inflammation Score | |
|---|---|---|---|
| | | 16th | 19th day |
| Control | — | 11.8 | 17.0 |
| KC-404 | 20 | 6.6** | 10.3*** |
| | 10 × 2 | 9.0 | 11.4** |
| Hydrocortisone | 5 | 8.1 | 9.3*** |

**$P < 0.02$,
***$P < 0.01$.

Experiment 2

The results of acute toxicological experiments were shown in Table 4.

TABLE 4

Acute Toxicity of KC-404 in Rats and Mice

| Species | Sex | $LD_{50}$ (mg/kg) | | | |
|---|---|---|---|---|---|
| | | i.v. | i.p. | s.c. | p.o. |
| Rat | Male | 43.2 | 500 | 1450 | 1340 |
| | Female | 42.5 | 419 | 1366 | 1396 |
| Mouse | Male | 160 | 460 | 3000 | 1880 |
| | Female | 146 | 500 | 3100 | 1860 |

What is claimed is:

1. A method of treatment for rheumatic diseases comprising administering an anti-rheumatic effective amount of 3-isobutyryl-2-isopropylpyrazolo[1,5-a]pyridine to a patient requiring such treatment.

2. The method of claim 1 wherein the amount of 3-isobutyryl-2-isopropylpyrazolo[1,5-a]pyridine is in the range from 1 to 500 mg.

* * * * *